United States Patent
Assouline et al.

(10) Patent No.: US 12,285,498 B2
(45) Date of Patent: Apr. 29, 2025

(54) PHARMACEUTICAL COMPOSITION WITH NANOPARTICLE-BASED DRUG DELIVERY COMBINED WITH NON-INVASIVE RADIOGRAPHIC MONITORING MODEL

(71) Applicant: NANOMEDTRIX, LLC, Coralville, IA (US)

(72) Inventors: Joe G Assouline, Coralville, IA (US); Sean K. Sweeney, Coralville, IA (US)

(73) Assignee: NANOMEDTRIX, LLC, Coralville, IA (US)

( * ) Notice: Subject to any disclaimer, the term of this patent is extended or adjusted under 35 U.S.C. 154(b) by 0 days.

(21) Appl. No.: 18/811,352

(22) Filed: Aug. 21, 2024

(65) Prior Publication Data

US 2025/0064987 A1 Feb. 27, 2025

Related U.S. Application Data

(63) Continuation of application No. 18/456,300, filed on Aug. 25, 2023, now Pat. No. 12,102,693.

(51) Int. Cl.

| | | |
|---|---|---|
| *A61K 9/51* | (2006.01) | |
| *A61K 9/00* | (2006.01) | |
| *A61K 31/00* | (2006.01) | |
| *A61K 31/337* | (2006.01) | |
| *A61K 31/407* | (2006.01) | |
| *A61K 31/704* | (2006.01) | |
| *A61K 31/7068* | (2006.01) | |
| *A61K 49/00* | (2006.01) | |
| *A61K 49/08* | (2006.01) | |
| *A61K 49/22* | (2006.01) | |
| *A61P 35/00* | (2006.01) | |

(52) U.S. Cl.
CPC ........ *A61K 49/0002* (2013.01); *A61K 9/0053* (2013.01); *A61K 9/5115* (2013.01); *A61K 31/337* (2013.01); *A61K 31/407* (2013.01); *A61K 31/658* (2023.05); *A61K 31/704* (2013.01); *A61K 31/7068* (2013.01); *A61K 49/0093* (2013.01); *A61K 49/085* (2013.01); *A61K 49/225* (2013.01); *A61P 35/00* (2018.01)

(58) Field of Classification Search
CPC .... A61K 5/5005; A61K 5/16; A61K 47/6851; A61K 9/51
See application file for complete search history.

(56) References Cited

U.S. PATENT DOCUMENTS

| | | |
|---|---|---|
| 2017/0291910 A1 | 10/2017 | Patil et al. |
| 2018/0194833 A1 | 7/2018 | Kallunki et al. |
| 2021/0113716 A1* | 4/2021 | Assouline ............... A61K 49/16 |
| 2023/0189773 A1 | 6/2023 | Gutmann et al. |

FOREIGN PATENT DOCUMENTS

WO WO-2017120537 A1 * 7/2017 ........... A61K 31/337

OTHER PUBLICATIONS

Balasubramanian et al, Adjuvant therapies for non-muscle-invasive bladder cancer: advances during BCG shortage, World Journal of Urology, Jan. 27, 2022, pp. 1111-1124, vol. 40, Springer Nature, Germany.

Bazarbashi et al, Recurrence and progression in nonmuscle invasive transitional cell carcinoma of urinary bladder treated with intravesical Bacillus Calmette-Guerin: A single center experience and analysis of prognostic factors., Urology Annals, Jul.-Sep. 2016, pp. 333-337, vol. 8, Issue 3, Wolters Kluwer—Medknow, India.

Cassell et al, Non-Muscle Invasive Bladder Cancer: A Review of the Current Trend in Africa, World Journal of Oncology, 2019, pp. 123-131, vol. 10(3), Elmer Press, Inc., Canada.

Celik et al, Anna Karenina principle in personalized treatment of bladder cancer according to oncogram: which drug for which patient?, Personalized Medicine, May 17, 2023, ISSN 1741-0541, Future Medicine Ltd, United Kingdom.

Chen et al, Thiolated Mesoporous Silica Nanoparticles as an Immunoadjuvant to Enhance Efficacy of Intravesical Chemotherapy for Bladder Cancer, Advanced Science, Jan. 13, 2023, pp. 1-14, ISSN 10: 2204643, Wiley-VCH GmbH, United States.

DeGraff et al, When Urothelial Differentiation Pathways Go Wrong: Implications for Bladder Cancer Development and Progression, Urologic Oncology: Seminars and Original Investigations, Aug. 2013, pp. 802-811, vol. 31(6), Elsevier Inc., Netherlands.

Fang et al, Diminishing the side effect of mitomycin C by using pH-sensitive liposomes: in vitro characterization and in vivo pharmacokinetics, Drug Design, Development and Therapy, 2018, pp. 159-169, vol. 12, Dove Medical Press Limited, United Kingdom.

Han et al, Emerging pro-drug and nano-drug strategies for gemcitabine-based cancer therapy, Asian Journal of Pharmaceutical Sciences, 2022, pp. 35-52, vol. 17(1), Elsevier B.V., Netherlands.

Igaz et al., Functionalized Mesoporous Silica Nanoparticles for Drug-Delivery to Multidrug-Resistant Cancer Cells, International Journal of Nanomedicine, Jul. 14, 2022, pp. 3079-3096, vol. 17, Dove Medical Press Limited, United Kingdom.

Kates et al, Phase 1/2 Trial Results of a Large Surface Area Microparticle Docetaxel for the Treatment of High-Risk Nonmuscle-Invasive Bladder Cancer, The Journal of Urology, Oct. 2022, pp. 821-829, vol. 208, Wolters Kluwer Health Inc., United States.

Konala et al, Immunotherapy in Bladder Cancer, American Journal of Therapeutics, 2022, pp. e334-e337, vol. 29(3), Wolters Kluwer Health, Inc., United States.

Lamm et al, Bacillus Calmette-Guerin and dinitrochlorobenzene immunotherapy of chemically induced bladder tumors, Investigative Urology, Mar. 1977, pp. 369-372, vol. 14(5), The Williams & Wilkins Co., United States.

(Continued)

*Primary Examiner* — Micah Paul Young
(74) *Attorney, Agent, or Firm* — SHUTTLEWORTH & INGERSOLL, PLC; Jason R. Sytsma

(57) ABSTRACT

A mesoporous silica nanoparticle ("MSN"); a bioactive agent loaded into the MSN and an enteric coating encapsulating the surface of the MSN for oral administration or combination with more than one other pharmaceutical composition each having distinct bioactive agents.

17 Claims, 4 Drawing Sheets

(56) References Cited

OTHER PUBLICATIONS

Li et al., Mitomycin C-Soybean Phosphatidylcholine Complex-Loaded Self-Assembled PEG-Lipid-PLA Hybrid Nanoparticles for Targeted Drug Delivery and Dual-Controlled Drug Release, Molecular Pharmaceutics, Jul. 2014, pp. 2915-2927, vol. 11(8), ACS Publications, United States.

Lichtenauer et al, On the growth of bladder carcinoma heterotransplants during administration of experimental chemotherapy, Der Urologe. Mar. 1967, pp. 93-99, vol. 6(2), Germany.

Manzano et al, Characterization of a Mesoporous Silica Nanoparticle Formulation Loaded with Mitomycin C Lipidic Prodrug (MLP) and In Vitro Comparison with a Clinical-Stage Liposomal Formulation of MLP, Pharmaceutics, Jul. 17, 2022, pp. 1483, vol. 14, MDPI, Switzerland.

O'Donnell et al, Combination Intravesical Therapy, Urologic Clinics of North America, Feb. 2020, pp. 83-91, vol. 47(1), Elsevier, United States.

Pei et al, A robust LC—MS/MS method for the simultaneous determination of docetaxel and voriconazole in rat plasma and its application to pharmacokinetic studies, Biomedical Chromatography, Mar. 2018, pp. e4246, vol. 32(8), John Wiley & Sons, Ltd., United States.

Pietzak et al, Next-generation Sequencing of Nonmuscle Invasive Bladder Cancer Reveals Potential Biomarkers and Rational Therapeutic Targets, European Urology, Dec. 2017, pp. 960-961, vol. 72(6), Elsevier, Netherlands.

Raza et al, DextranPLGAloadeddocetaxel micelles with enhanced cytotoxicityand better pharmacokinetic profile, International Journal of Biological Macromolecules, Mar. 2016, pp. 206-212, vol. 88, Elsevier, Netherlands.

Ryan et al, Gemcitabine in the treatment of bladder cancer, Expert Opinion on Pharmacotherapy, 2000, pp. 547-553, vol. 1(3), Ashley Publications Ltd., United States.

Steinberg et al, Combination Intravesical Chemotherapy for Non-muscle-invasive Bladder Cancer, European Urology Focus, Jul. 6, 2018. pp. 503-505, vol. 4(4), Elsevier B.V., Netherlands.

Stricker et al, Bacillus Calmette-Guerin Plus Intravesical Interferon ALPHA-2b in Patients With Superficial Bladder Cancer, Urology, Mar. 6, 1996, pp. 957-961, vol. 48(6), Elsevier Science Inc., Netherlands.

Sun et al, A Pharmacokinetic and Pharmacodynamic Evaluation of the Anti-Hepatocellular Carcinoma Compound 4-N-Carbobenzoxy-gemcitabine (Cbz-dFdC), Molecules (Basel, Switzerland), May 8, 2020, pp. 2218, vol. 25(9), MDPI, Switzerland.

Swanson et al, Bladder Cancer Advocacy Network, Newsletter. Sep. 2020.

Takahashi et al, Increased Antitumor Activity in Combined Treatment TS-1 and Docetaxel, Oncology, Jul. 4, 2005, pp. 130-137, vol. 68(2-3), S. Karger AG, Basel, Switzerland.

Teoh et al, Recurrence mechanisms of non-muscle-invasive bladder cancer—a clinical perspective, Nature Reviews Urology, May 2022, pp. 280-294, vol. 19(5), Springer Nature Limited, London.

Turner et al, Oral Gavage in Rats: Animal Welfare Evaluation, Journal of the American Association for Laboratory Animal Science, Jan. 2012, pp. 25-30, vol. 51(1), American Association for Laboratory Animal Science, United States.

Wang et al, Development and validation of a UPLC—MS/MS assay for the determination of gemcitabine and its L-carnitine ester derivative in rat plasma and its application in oral pharmacokinetics, Asian Journal of Pharmaceutical Sciences, Jan. 9, 2017, pp. 478-485, vol. 12(5), Elsevier B.V., Netherlands.

Yin et al, Comparative pharmacokinetic study of PEGylated gemcitabine and gemcitabine in rats by LC-MS/MS coupled with pre-column derivatization and MSALL technique, Talanta, 2020, vol. 206, Elsevier, Netherlands.

Zhang et al, Sample Extraction and Simultaneous Chromatographic Quantitation of Doxorubicin and Mitomycin C Following Drug Combination Delivery in Nanoparticles to Tumor-bearing Mice, Journal of Visualized Experiments, Oct. 5, 2017, vol. 128, pp. e56159, Journal of Visualized Experiments, United States.

* cited by examiner

PHARMACEUTICAL COMPOSITION WITH NANOPARTICLE-BASED DRUG DELIVERY COMBINED WITH NON-INVASIVE RADIOGRAPHIC MONITORING MODEL

STATEMENT REGARDING FEDERALLY SPONSORED RESEARCH

This invention was made with government support under 1R43CA232778-01 and 2R44CA232778-02A1 awarded by the National Institutes of Health, National Cancer Institute, and Small Business Innovation Research (SBIR). The government may have certain rights in the invention.

CROSS-REFERENCE TO RELATED APPLICATIONS

This present application is a continuation of U.S. patent application Ser. No. 18/456,300 filed Aug. 25, 2023, the contents of which are incorporated herein by reference.

BACKGROUND INFORMATION

Bladder cancer or urothelial cancer is one of the most diagnosed and lethal cancers in the United States. Currently, treatment involves either a partial or radical cystectomy combined with chemotherapy or BCG treatment. These methods are painful and can lead to a decreased quality of life for the patient. As an alternative, mesoporous silica nanoparticles (MSN) may be used to deliver chemotherapy drug straight to the tumor. This can decrease the exposure of chemotherapy drugs to healthy cells while delivering an increased payload to cancerous cells. There is a need for the development of a non-invasive method to remotely evaluate and quantitate the impact of anti-tumor nanodrug delivery. Recent laboratory animal costs, increased regulations, decrease in professional staff and funding, demand novel methods to evaluated pharmacological materials for the treatment of cancer. Murine models have been widely used; however, mice models are fraught with technical difficulties (genetic and technical/physical inherent difficulties. A larger rodent experimental animal is warranted because it is cost-effective and expeditious compared to the canine model with extensive related regulatory issues. In addition, xenograft experimentation using human cancer cells is attainable in rodent models. Mice are arguably too small to collect repeated samples for pharmacokinetics/pharmacodynamics (PK/PD) and procurement of detailed imaging data to monitor bio-effectiveness of the nanodrug delivery. In this disclosure, we document a rat model for bladder cancer and options for a rat athymic model.

We previously reported the invention of an MSN that provides imaging contrast when using magnetic resonance imaging (MRI), computed x-ray tomography (CT), high resolution ultrasound imaging (HRUS), or fluorescent imaging modalities, alone or in combination, which can be used for non-invasive bladder cancer monitoring (US 2015/0125398 A1). We subsequently disclosed additional features to the same particle, providing evidence for loading and controlled release of conventional chemotherapeutic agents administered intravesically (in the bladder via a catheter), thereby improving dwell time and bladder cancer outcomes (U.S. patent application Ser. No. 17/069,531, accepted), the contents of which are hereby incorporated by reference herein.

Given the same tumor implantation (verified by imaging), animals respond variably, from no response (tumor continues growing) to complete remissions. This is a testament to the potential benefits of personalized/precision medicine and gives credibility to the choice of therapeutic regimen in each patient. Ultimately, knowledge of the most effective combination of drugs will enhance efficacy and safety while decreasing toxicity a patient regimen management. In addition, this information is supported by our bioinformatic and genomic comparative retrospective studies.

Traditionally, the preferred treatment for BL or urothelial carcinoma (transitional cell carcinoma) has been intravesicular BCG injection since 1976 (Lamm, Invest Urol. 14(5):369-72). This treatment has been highly successful and continues to be [the rate of recurrence is 30-45% (Bazarbashi, Urol Ann. 8(3): 333-337)]. However, it is effective only on non-muscle invasive tumors (NMIBC) [70-75% of BL compared to muscle invasive (Cassell, World J Oncol. 10(3): 123-131.)]. In the muscle invasive version of the cancer, tumor cells penetrate the superficial layer to reach the vascularized smooth muscle layer, giving access systemic distribution of cancerous cells. The locally administered treatment does not address the potentially devastating metastatic risks starting when tumor cells reach the vascularized detrusor muscular layer (DeGraff, Urol Oncol. 31(6): 802-11; Teoh, Nat Rev Urol. 19(5):280-294).

Additionally, a recent and ongoing shortage of BCG preparations, due to high demand and manufacturing concerns, has forced rationing and moving otherwise qualified patients to other treatments (Swanson, https://bcan.org/wp-content/uploads/2020/09/2020-joint-letter-re-BCG-short-age-with-signatures-and-logos-FINAL-BCAN.pdf; Balasubramanian, World J Urol. 40(5):1111-1124). Presently, several drugs are investigated and have shown clear effectiveness in BL. One of the most potent therapies is Docetaxel (DOC) but some other chemotherapeutic drugs have long been available: interferon (IFN; Stricker, Urology, 48(6):957-996), GEM (Ryan, Expert Opin Pharmacother. 1(3):547-53), and MMC (Lichtenauer, Urologe. 6(2):93-9.). The new investigational immunotherapies in conjunction with combination therapies have shown success (Konala, Am J Ther. 2022 May-June; 29(3):e334-e337.). However, combination therapies are impracticable because of timing drugs, interactions, solubility, and dispersion disparity between drug requirements/specs (Steinberg, Eur Urol Focus. 2018 July; 4(4):503-505.).

A novel formulation of DOC (NanoDoce) showed better penetration of the tumor and bladder wall than drug alone. The molecule consists of a large surface area microparticle (LSAM) docetaxel and is produced using submicron (900 nm) particle production technology. Compared with an equivalent dose of conventional drug, the tumor showed a similar reduction in growth compared to the untreated controls, and more significantly the growth reduction was sustained longer after the end of the treatment cycle. In the Phase 1/11 clinical trial, 19 patients received intratumoral injections of NanoDoce at the time of resection followed by an intravesical injection. The treatment regimen was well-tolerated with minimal drug infiltrating the bloodstream and induction of an anti-tumor immune response (https://nanology.us/development/clinical-programs-2/). Kates et al published their findings of a Phase 1/2 clinical trial of NanoDoce (Kates, J Urol. 208(4):821-829. (https://pubmed.ncbi.nlm.nih.gov/35574612/).

Gemcitabine (GEM) is a well-known molecule despite poor pharmacokinetics. Improvement of the drug delivery efficiency as reviewed by Han et al (Asian J Pharm Sci. 17(1): 35-52.). Prodrugs and nanoparticle delivery strategies have been attempted, yet only marginal improvements have been seen. Silica-based nanoparticles for drug delivery and biomedical applications have been well documented, however it was reported that while hydrophilic gemcitabine is poorly encapsulated directly in MSN (FIG. 1), its lipophilic pro-drug formation is more readily loaded. The prodrug lauroylgemcitabine could be effectively loaded into MSNs to protect GEM from rapid plasmatic metabolization physically and chemically. However, compared to GEM, MSNs loading lauroyl-gemcitabine showed less cytotoxicity to MDAMB-231 cells and human ovarian cancer cell (A2780 cells) due to the slow and gradual drug release.

Mitomycin c (MMC) is also well-characterized as a candidate for drug delivery. In one study, Zhang et al compared free drug with a polymer MMC conjugate in mice bearing human breast cancer xenografts (Zhang, Jove, 5 Oct. 2017, 128). In this paper, the focus is on the HPLC detection method, and the biodegradable polymer is not well described. However, it is shown to be a mixture of PEG molecules mixed in an emulsion of MMC. Injected intravenously, the conjugates are retained longer in the bloodstream than free MMC, and more MMC is detected within the tumors of mice injected with the MMC conjugate than the MMC alone. Furthermore, Chen et al have recently developed a mucoadhesive MSN particle loaded with MMC for the treatment of bladder cancer [Adv Sci (Weinh). 10(7): 2204643]. In their orthotopic model, they used GFP mouse bladder tumor cells and in vivo imaging systems (IVIS) to quantify the tumors. Although no release or pharmacokinetics were performed in the animals, the anti-tumor effect of MMC was shown by tumor shrinkage, which was further enhanced using the mucoadhesive MSN. Igaz et al demonstrated anti-tumor activity and overcoming of multi-drug resistance in vitro by using MSN loaded with MMC (Int J Nanomedicine. 17: 3079-3096). Manzano et al loaded MSN with a lipophilic prodrug MMC formulation called Promitil® to overcome the challenges of free MMC (Pharmaceutics. 14(7): 1483). Like Igaz, Manzano demonstrated drug release and anti-tumor activity in vitro, stopping short of in vivo studies.

Other drugs could be used in combination through our materials, having a molecular weight and solubility compatible with nano-particle loading and delivery: valrubicin, cabazitaxel, Adriamycin.

Enabling personalized medicine: it is a fact that patients respond differently to drug therapy. Given the same treatments, some tumors regress while others are unresponsive. There is a growing interest and opportunity to personalize NMIBC care through genomics. Our materials and methods corroborate and demonstrate this notion. In our experiments, given the same drug treatment, results varied widely. Our PK studies show consistency of drug dosage and delivery and nevertheless varied effectiveness. Best results were obtained in combination of drugs and mode of presentation (oral vs. intravesicular).

SUMMARY

In accordance with one aspect of the present invention, disclosed is an orally administered pharmaceutical composition comprising: a mesoporous silica nanoparticle ("MSN"); a bioactive agent loaded into the MSN; and an enteric coating encapsulating the surface of the MSN. Because the pharmaceutical composition comprises of these components, it can be administered singularly or in combination with more than one other pharmaceutical composition each having distinct bioactive agents administered in different manners; for example, orally and intravesically with the first coating comprises enteric coating and the second coating comprises a gelatin, polymer, or a synthetic phospholipid bilayer. This allows the pharmaceutical compositions to be administered concurrently such that non-invasive and invasive tumors are addressed sequentially or substantially concurrently.

In an embodiment, the MSN is less than or equal to 200 nm in diameter with a mean pore diameter of about 2-3.8 nm for loading the bioactive agent, which can comprise any chemotherapeutic agent or an immunogenic substance. In an embodiment, the bioactive agent is selected from the group consisting of cannabidiol, epirubicin, mitomycin-c, gemcitabine, and taxols (docetaxel).

In an embodiment, the pharmaceutical composition can comprise of a contrast agent covalently linked to the MSN to allow for non-invasive monitoring of tumor growth. The contrast agent can comprise of or consist of at least one of a heavy metal, gadolinium, lanthanide, a fluorophore, and a surface modification agent detectable with ultrasound.

In an embodiment, the MSN can be covalently linked to a targeting peptide or an amino acid. The targeting peptide or amino acid can be any cancer cell specific peptide or acid and correlated with the bioactive agent; for example, the bladder cancer cell specific cyclic peptide (Cyc6). It should be noted that this is optional.

The foregoing pharmaceutical compositions have utility, for example, in a method of treatment of a tumor comprising the steps of: administering to a patient a first pharmaceutical composition and a second pharmaceutical composition; wherein the first pharmaceutical composition comprises a mesoporous silica nanoparticle ("MSN"), a first bioactive agent loaded into the MSN, a first coating encapsulating the surface of the MSN, and a targeting peptide or an amino acid covalently linked to the MSN; wherein the second pharmaceutical composition comprises an MSN, a second bioactive agent loaded into the MSN, a second coating encapsulating the MSN, and a targeting peptide or an amino acid covalently linked to the MSN; and wherein the first bioactive agent is distinct from the second bioactive agent.

In other embodiments, the pharmaceutical composition has utility in a method for real-time testing and monitoring of tumor growth in a athymic xenograft animal model comprising: administering to the athymic xenograft animal model a first pharmaceutical comprising a mesoporous silica nanoparticle ("MSN"), a first bioactive agent loaded into the MSN, a first coating encapsulating the surface of the MSN, a targeting peptide or an amino acid covalently linked to the MSN, and a contrast agent covalently linked to the MSN; and monitoring non-invasively a size of a tumor by detecting the first pharmaceutical composition by the contrast agent, wherein the athymic xenograft animal model can be a rat model.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
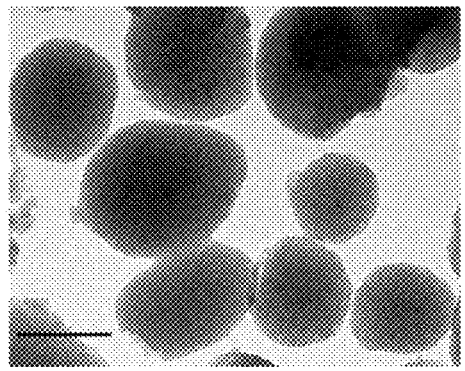
FIG. 1 shows a typical transmission electron micrograph of MSN particles. Scale bar=200 nm. The mean pore diameter is 3.8 nm as measured by Barret-Joyner-Halenda pore size analysis, which provides physical space for loading spherical molecules up to ~75 kDa. For reference, bladder cancer standards of care, DOC/MMC/GEM are under 1 kDa.
Figure 2:
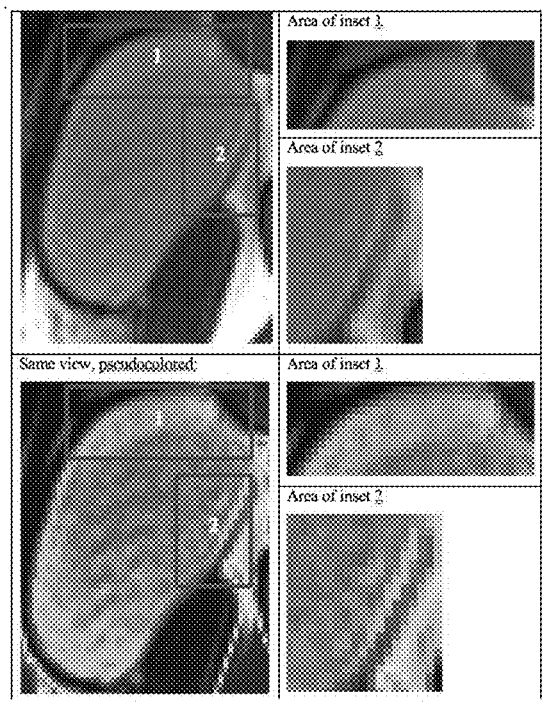
FIG. 2 shows Proof of penetration of particles to deeper layers; pseudocolor 3D renderings of normal rat bladder with specific sections of bladder wall/detrusor highlighted for analysis. Around most of the bladder, this wall/detrusor section is routinely 2-3 voxels wide.
Figure 3:
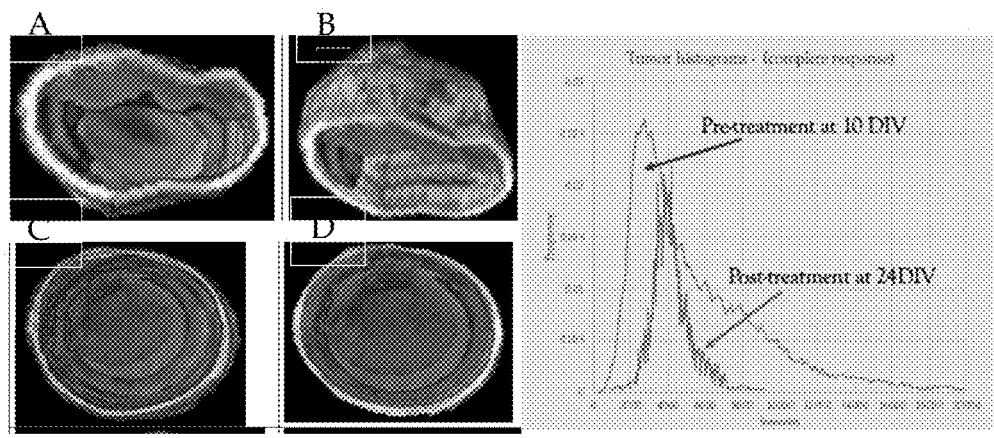
FIG. 3 shows examples of Rat Bladder Cancer. Instilled tumor treatment with MSN-Chemotherapy; shows MRI imaging of Rat model with BL. A-B) Tumor was confirmed on day 7 following instillation and reached a maximum of 36.7 mm$^3$. C-D) a complete response was observed following 24 days and 3 rounds of treatments.

Here, we disclose a preclinical model of intravesicular targeted nanoparticle anti-cancer treatment which can be supplemented by oral enteric nano-particle-abled delivery. As this is time-critical cancer, a maximum tumoricidal dose as well as multiple combined drugs must be administered. However to date, clinically this multi-dose of different drugs approach is challenging and needs to test pre-clinically (in animal models). As a prototype: rat model of bladder cancer (BC) in which following tumor instillation, repeated/sequential imaging data acquisition (MRI and US) will be used to simultaneously correlate and monitor tumor growth with real-time PK measurements (LC-MS). Our data exhibit the ability to instill bladder cancer (BC) tumor (as a prototype) in a normal or athymic rats and subsequently, non-invasively monitor growth changes both with imaging and/or biochemically.

We conducted experiments to demonstrate simultaneous instillation of combination or sequential therapies [combination Gemcitabine (GEM)-MSN/Mitomycin-C (MMC)-MSN/Docetaxel (DOC)-MSN]. Each drug is loaded separately in MSN and the drug-MSN particles are blended prior to instillation and/or ingestion. In addition, we show that intravesicular, oral and blends/permutations are achievable and beneficial. We also document efficacy and susceptibility individual differences for each animal.

A rat xenograft model of human bladder cancer will help understand the pathobiology of bladder cancer as well as to ascertain the potential of medical imaging as a remote assessment tool in the treatment of cancer. The success of this method enhances support for the use of this model for other forms of cancer i.e., colorectal glioma and small cell lung carcinoma.

We developed a model mimicking and replicating clinical settings, circumstances and the treatment based on current standard of care. Dosages for this rodent model are commensurate with the weight of hemodynamic consideration. Unique attributes of this discovery are that the treatment includes specially designed and manufactured multi-functional nanoparticles. This material allows for a non-invasive monitoring of the tumor behavior and simultaneous combination drug treatment. In bladder cancer, our discovery and this disclosure allows for the delivery of particles intravesically (in the bladder via catheter). The shielding and targeting attributes of the specially designed particles, which were disclosed previously in art disclosures in U.S. Patent Publication Nos. 2015/0125398 and 2021/0113716 (the contents of which are hereby incorporated by reference herein), have an inherent delay in delivering the drugs preferentially to the tumor (with limited off-target binding) and penetrate the tumor deeper than any other material available to date. In addition, differing from current standard of care [local *bacillus* Calmette-Guerin (BCG) superficial tumor treatment], the described material released the lethal drugs to the deeper muscular layer of the bladder wall. Penetration to the muscular layer is an indication of more invasive and expanding cancerous invasion (DeGraff, Urol Oncol. 31(6):802-11; Teoh, Nat Rev Urol. 19(5):280-294). This more advanced stage of the cancer heralds the possibility of dissemination of the cancer and the formation of metastatic foci, all of which demands a more stringent chemotherapeutic treatment and possibly cystectomy (partial or radical removal of the bladder). To understand, evaluate, and quantify any new therapeutic strategy, an in vivo model must be used. This disclosure describes a model exquisitely suited for the purpose:

1) That a rat model or other athymic xenograft animal is feasible for the experiment of intravesicular instillation of a homolog (and may be xenografting);
2) Demonstrate through non-invasive imaging techniques, the extent of the penetration of the drug-MSN into the tumor as it infiltrates the deep layers of bladder including detrusor muscle; a crucial therapeutic determinant of the muscle invasive form of the disease;
3) That the monitoring of the growth for untreated subject animals, and effectiveness on growth reduction following treatment, can be ascertained accurately/numerically documented non-invasively and repeatedly in the same animal. Computational imaging of our particles-co synthesized with contrast agents, thus enhancing the signal (prior art disclosure);
4) That the treatment is effective in reducing or eliminating the tumor (bladder cancer);
5) Intravesicular treatment allows for a combination of drugs (among the current standard of care: GEM, MMC, and DOC), causing overwhelming toxic response;
6) That an oral presentation of a modified nanoparticle-drug treatment is a potential novel option for the treatment of BL (as evidence by growth reduction and PK of drug in the urine) and as an anti-metastatic prevention/treatment;
7) The supplementation of oral and intravesicular presentation of the combined drugs is more effective and less toxic in the MSN presentation compared to drugs alone; and
8) An important model to demonstrate individual differences in response to the treatment.

Rat models are highly advantageous for efficacy and pharmacokinetic studies, due to their larger compared to mice. For such pharmacokinetic studies, the drugs concentration introduced by various routes, may be used to determine on and off target drug delivery. In addition, non-invasive imaging techniques such as magnetic resonance imaging (MRI) and ultrasound (US) may be used to monitor the growth and fate of the tumor within rat bladder to adjust treatment regimens.

The MSN can have a contrast agent covalently linked to the MSN to assist with non-invasive imaging techniques. The contrast agent comprises at least one of a heavy metal, gadolinium, lanthanide, a fluorophore, and a surface modification agent detectable with ultrasound. Alternatively, the contrast agent can be selected from the group consisting of a heavy metal, gadolinium, lanthanide, a fluorophore, and a surface modification agent detectable with ultrasound.

Adult female rats are 250-300 g in body weight, or 10-15 times larger than adult C57-Bl6 mice. The volume of an aqueous solution given by oral gavage procedure can be up to 5 mL/kg, thus for a 300 g rat, 1.5 mL volume is achievable (Turner, J Am Assoc Lab Anim Sci. 51(1): 25-30.). This permits a mass of 150 mg MSN, or the equivalent dose of free drug. The recommended volume of a tail vein injection is also 5 mL/kg, thus 150 mg MSN or equivalent drug can be administered by i.v. as well (https://research.unc.edu/files/2020/12/rat-handling-and-techniques.pdf).

We took advantage of the larger size of rats (compared to mice) to collect sufficient sample to generate PK/PD data after administration of the chemotherapeutic cocktail GEM, DOC, and MMC. We used similar dosage and regimen described as the basis for testing in canine subjects. Table 1 shows an example calculation of drug loading/dosages for Gem, Doc, and MMC loaded in MSN material.

TABLE 1

| Agent | Systemic Dose | Rat Dosage (300 g body wt) | MSN loading (mg drug per mg MSN) | Quantity of drug-loaded MSN |
|---|---|---|---|---|
| Gem | 120 mg/kg | 36 mg | 0.6 | 6 mg |
| Doc | 30 mg/kg | 9 mg | 0.15 | 6 mg |
| MMC | 4.5 mg/kg | 1.35 mg | 0.3 | 4.5 mg |

Blood, urine, and stools were collected to evaluate renal and gastro-intestinal clearance of nanomaterials. Sequential and simultaneous administration of one material and before the start of another to allow full clearance. At the end of all tests the rats were be euthanized to collect bladder, kidneys, and liver to measure accumulation of material (data not shown).

While the bioactive agents used in the rat model include (either singularly or in combination), Gemcitabine (GEM), Mitomycin-C (MMC), and Docetaxel (DOC), those skilled in the art will recognize that the chemotherapeutic bioactive agents can include any drugs that are included in the current standard of care for the treatment of any cancers, such as cannabidiol, epirubicin, and other taxols. While in this disclosure only chemotherapeutic drugs were used, other agents such as immunogenic agents and drugs could be loaded into MSN and delivered in a similar manner.

The combination and benefits of using shielded or encapsulated particles to administer the multiple chemo drugs simultaneously without potential drug chemical interference/toxicity is disclosed. In this regard, a first pharmaceutical composition comprising a first MSN, a first bioactive agent loaded into the first MSN, an enteric coating encapsulating the surface of the first MSN can be combined with a second pharmaceutical composition comprising a second MSN, a second bioactive agent loaded into the second MSN, and an enteric coating encapsulating the surface of the second MSN. The combination of the first pharmaceutical composition and the second pharmaceutical composition can be by way of a single pill for oral delivery or liquid form. Each or one of the first and second pharmaceutical compositions can comprise a targeting peptide or an amino acid covalently linked to the first MSN; for example, a bladder cancer cell specific peptide (Cyc6). This allows the first pharmaceutical composition to be administered orally and the second pharmaceutical composition to be administered intravesically, for example. In this way, the first coating can comprise enteric coating and the second coating comprises a gelatin, polymer, or a synthetic phospholipid bilayer. The administration of the first pharmaceutical composition and the second pharmaceutical composition can be administered concurrently such that non-invasive and invasive tumors are addressed sequentially or substantially concurrently. More specifically, the dosage and frequency of treatment varies to adjust with disease staging. In rat experimentation in this disclosure, chemotherapeutic rounds of treatment cycles MSN-drugs treatments were administrated 3 times weekly for 3 weeks (with planned MRI monitoring). Each treatment was a combination Gem-MSN/MMC-MSN/Doc-MSN either per-oral or intravascularly. Body fluids were collected at scheduled intervals. The first pharmaceutical composition and the second pharmaceutical composition each can comprise a contrast agent covalently linked to the MSN to aid imaging to monitor disease progression. This allows for non-invasively monitoring a size of a tumor by imaging the first pharmaceutical composition and the second pharmaceutical composition as each are metabolized.

Such drugs (i.e., bioactive agents) can included Gem-MSN/MMC-MSN/Doc-MSN, P.O., for muscle invasive bladder cancer. Our experimentation shows great advantages in shielding and encapsulation of the drug within MSN compared to drug alone. We have evidence that intravesicular treatment and oral presentation of the simultaneous multiple drug treatment results in reduced toxicity (compared to drug alone) and better retention following delayed release (see PK studies).

Detail of tumor instillations (Rat-tumor into-rat) this section demonstrate that we can detect each drugs in fluids and the drugs are actively destroying the tumor Female rats in this experimentation were either Fischer F344 (normal strain), a strain widely used in gerontology and carcinogenicity testing programs, or athymic nude rats (Hsd:RH-Foxn1$^{rnu}$), a strain commonly used when human tissue xenografts are needed for study. Both strains were obtained from Inotiv (Indianapolis, IN, USA). F344 rats were instilled with rat AY27 bladder cancer cells and athymic nude rats were instilled with human male bladder cancer strains: T24 and UMUC-3. After confirmation of tumor growth, rats were subjected to either intravesical or oral treatments, with blood/urine collected at prescribed timepoints for PK/PD studies. In cases in which the tumor grew out of control, treatment was switched to combination intravesical and oral. In these rats, blood/urine were collected, but spared from PK/PD studies to avoid confounding results. In this cohort, rats (n=3) were instilled with tumors and treated with sequential intravesical and oral drug-MSN 3-drugs load and body fluids (blood/urine) collection at the same prescribed time points. An example: four rounds of treatment were administered fluid collected n=3 samples at each time point.

Figure 5:
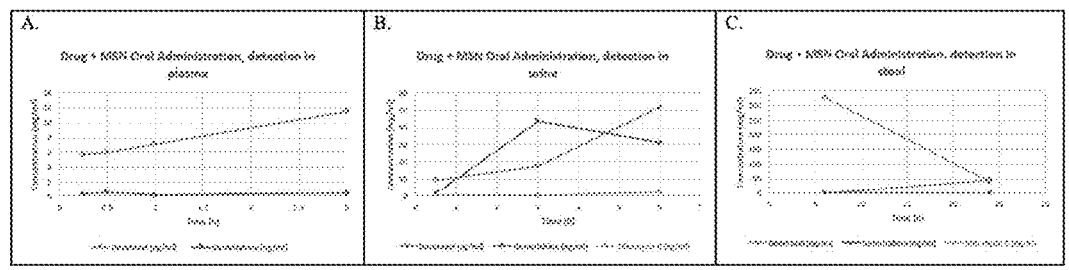
FIG. 5 shows PK parameters for drug-MSN administered orally. (A) In plasma, Cmax values are 0.6 ng/mL for Gemcitabine and 11.5 ng/mL for docetaxel, with tmax values of 30 minutes at 3 hours, respectively. Mitomycin C was not detected within the plasma. (B) In urine, Gemcitabine had a Cmax of 43.52 ng/mL and a tmax of 3 hours, Docetaxel reached a Cmax of 51.8 ng/mL and a tmax of 6 hours, and mitomycin c reached Cmax of 2.2 ng/mL with a tmax of 6 hours. (C) In the stool, Gemcitabine had a Cmax of 0.5 ng/mL and a tmax of 6 hours, Docetaxel reached a Cmax of 44.57 ng/mL and a tmax of 24 hours, and mitomycin c reached Cmax of 327.4 ng/mL with a tmax of 6 hours.
Figure 6:
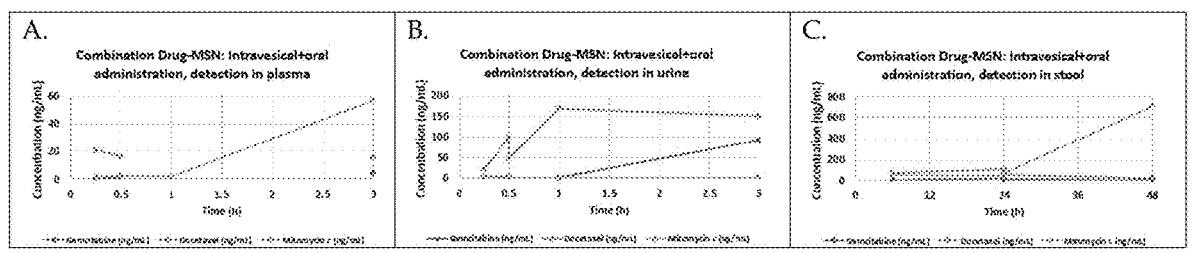
FIG. 6 shows the plasma concentration curves of the drugs.
Figure 7:
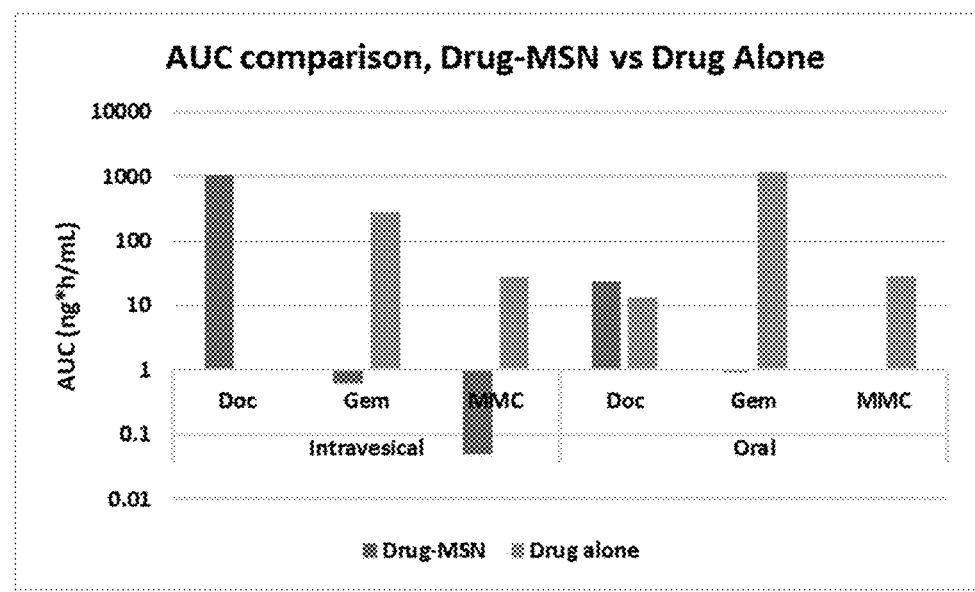
FIG. 7 shows a comparison of areas under the curve (AUC) for drug-MSN versus drug administered alone.

The following disclosed PK rat model studies. As a proof of drug release in the model we performed PK studies on orally administered docetaxel, gemcitabine, and mitomycin c loaded MSN were conducted in female F344 Fischer (normal) rats. Tables 2-4 summarize the PK parameters calculated, while FIGS. 5-7 show the concentration curves of the drugs. Table 2 shows a summary of pharmacokinetic parameters in athymic rats receiving oral treatment of drug loaded MSN:

TABLE 2

| Parameter | Docetaxel | Gemcitabine | Mitomycin C |
|---|---|---|---|
| Dose (mg) | 0.6 | 2.4 | 1.2 |
| $C_{max,plasma}$ (ng/ml) | 11.5 | 0.6 | n/a |
| $t_{max,plasma}$ (h) | 3 | 0.5 | n/a |
| Plasma Clearance (L/h) | 25.65 | 2560.00 | n/a |

TABLE 2-continued

| Parameter | Docetaxel | Gemcitabine | Mitomycin C |
|---|---|---|---|
| Plasma AUC (mg * h/L) | 0.0234 | $0.938 * 10^{-3}$ | n/a |
| $C_{max,urine}$ (ng/ml) | 51.8 | 43.52 | 2.2 |
| $t_{max,urine}$ (h) | 6 | 3 | 6 |
| $C_{max,stool}$ (ng/ml) | 44.57 | 0.5 | 327.4 |
| $t_{max,stool}$ (h) | 24 | 6 | 6 |

Table 3 shows a summary of pharmacokinetic parameters in athymic rats. In this experiment, following intravesical drug instillation, the treatment was supplemented by an oral treatment of drug loaded MSN:

TABLE 3

| Parameter | Docetaxel | Gemcitabine | Mitomycin C |
|---|---|---|---|
| Dose (mg) | 0.6 | 2.4 | 1.2 |
| $C_{max,plasma}$ (ng/ml) | 20.88 | 4.33 | 56.67 |
| $t_{max,plasma}$ (h) | 0.25 | 3 | 3 |
| Plasma Clearance (L/h) | 13.55 | 328.77 | 20.08 |
| Plasma AUC (mg * h/L) | 0.0443 | 0.0073 | 0.0598 |
| $C_{max,urine}$ (ng/ml) | 167.46 | 91.96 | 3.73 |
| $t_{max,urine}$ (h) | 1 | 3 | 0.5 |
| $C_{max,stool}$ (ng/ml) | 76.97 | 9.77 | 52.47 |
| $t_{max,stool}$ (h) | 24 | 24 | 24 |

Table 4 shows PK Parameters following oral administration of gemcitabine loaded MSN with escalating doses:

TABLE 4

| Dose | 0 mg | 133 mg | 267 mg | 400 mg |
|---|---|---|---|---|
| $C_{max,plasma}$ | 0 mg/ml | 2.05 ng/ml | 3.87 ng/ml | 5.67 ng/ml |
| $t_{max,plasma}$ | n/a | 0.5 h | 1 h | 0.5 h |
| $C_{max,urine}$ | n/a | 18.47 ng/ml | n/a | n/a |
| $t_{max,urine}$ | n/a | 1 h | n/a | n/a |
| $AUC_{plasma}$ | n/a | 5.13 ng * h/mL | 10.13 ng * h/mL | 13.75 ng * h/mL |
| Clearance | n/a | 25909.09 L/h | 26348.68 L/h | 29082.096 L/h |

Concentrations of mitomycin c within the plasma were below the level of detection. Although, a high concentration was noted within the stool, indicating a majority of the drug was excreted. In addition, low concentration of gemcitabine and docetaxel were found in the plasma, with higher levels found within the urine. The observed concentrations overall appear lower compared to other studies using systemic delivery. Orally administered MSN has delayed distribution and destination which may represent a selective absorption/mode of action with potentially critical/therapeutic benefits.

PK studies conducted in normal rats with combined intravesical and oral administrations of a admixture particles containing either docetaxel, gemcitabine, or mitomycin c loaded MSN. Table 3, shown above, summarizes the PK parameters calculated, while FIG. 6 shows the plasma concentration curves of the drugs. High concentrations of gemcitabine and docetaxel were found within the urine and stool, and a high concentration of mitomycin c was found within the plasma and the stool.

The area under the curve (AUC), a discrete integral of the plasma concentration of drug over time, is a better metric than simple Cmax/Tmax to show the overall duration of circulation of the drug in the bloodstream. When comparing the AUCs for drug loaded in MSN versus drug alone, AUC increases for docetaxel by 4 orders of magnitude in the case of intravesical administration and by 76% in the case of oral administration. The AUCs for Gemcitabine and Mitomycin C were higher for drug alone than they were for the drug-loaded MSN. An improvement of the AUC for Docetaxel is a positive result, as Doc and Gem are both known to have very low oral bioavailability (10%) and any improvement to the dwell time of either is most welcome. Thus, combined drugs are most effective (and potential less toxic in the msn presentation) since limited toxic effects (as evidenced by co-morbidity signs or death observed) compared to drugs alone.

The following discloses intravesical administration detection of the drugs delivered in the bladder: Cmax values are highest by multiple orders of magnitude in the urine 15 minutes following administration (Tables 5-7). More specifically, Table 5 shows a comparison of PK parameters for DOC from this and other studies:

TABLE 5

| Dosage | Administration Route | $C_{max}$ | $t_{max}$ | Clearance | AUC (Plasma Curves) (mg * h/L) | Reference |
|---|---|---|---|---|---|---|
| 3 mg/kg | Intravesical | n/a | n/a | n/a | n/a | Current Study |
| 3 mg/kg | Oral | 10.64 ng/ml | 1 h | 45.11 L/h | 0.0133 mg * h/L | Current Study |
| 3 mg/kg | Intravenous | 115.94 ng/ml | 0.25 h | 37.45 L/h | 0.016 mg * h/L | Current Study |
| 3 mg/kg | Intravesical, Drug-loaded MSN | 967.75 ng/ml | 0.5 h | 0.558 L/h | 1.078 mg * h/L | Current Study |
| 3 mg/kg | Oral, Drug-loaded MSN | 11.5 ng/ml | 3 h | 25.65 L/h | 0.0234 mg * h/L | Current Study |
| 3 mg/kg | Intravesical + Oral, Drug-loaded MSN | 20.88 ng/ml | 0.25 h | 13.55 L/h | 0.0443 mg * h/L | Current Study |
| 2 mg/kg-8 mg/kg | Intravenous | 68 ± 10 ng/ml (2 mg/kg) 7 µg/ml (5 mg/kg) 950 ng/ml (8 mg/kg) | 0.25 h (all doses) | 4293.49 L/h/m² (2 mg/kg) 0.182 L/h/m² (5 mg/kg) 8923.76 L/h/m² (8 mg/kg) | 0.277 mg * h/L (2 mg/kg) 16367.39 mg * h/L (5 mg/k) 2.2 ± 0.3 mg * h/L (8 mg/kg) | Takahashi, Pei, Raza |
| 5 mg/kg | Intravenous Drug-loaded Micelle | 11 µg/ml | 0.25 h | 2.46 L/h/m² | 1206 mg * h/L | Raza |

Table 6 shows a comparison of PK parameters for GEM from this and other studies.

TABLE 6

| Dosage | Administration Route | $C_{max}$ | $t_{max}$ | Clearance | AUC (Plasma Curves) | Reference |
|---|---|---|---|---|---|---|
| 12 mg/kg | Intravesical | 516.22 ng/ml | 0.25 h | 8.569 L/h | 0.280 mg * h/L | Current Study |
| 12 mg/kg | Oral | 636.02 ng/ml | 0.5 h | 2.109 L/h | 1.138 mg * h/L | Current Study |
| 12 mg/kg | Intravenous | 1791.59 ng/ml | 0.25 h | 1.042 L/h | 2.304 mg * h/L | Current Study |
| 12 mg/kg | Intravesical, Drug-loaded MSN | 0.42 ng/ml | 0.25 h | 3902.44 L/h | $0.615 * 10^{-3}$ mg * h/L | Current Study |
| 12 mg/kg | Oral, Drug-loaded MSN | 0.6 ng/ml | 0.5 h | 2560.00 L/h | $0.938 * 10^{-3}$ mg * h/L | Current Study |
| 12 mg/kg | Intravesical + Oral, Drug-loaded MSN | 4.33 ng/ml | 3 h | 328.77 L/h | 0.0073 mg * h/L | Current Study |
| 15-50 mg/kg | Intravenous | 14145 ± 4115 ng/ml 39.5 ± 5.93 ug/ml 2658.04 ± 1212.6 ng/ml | 0.083 h (15-20 mg/kg) 1 h (50 mg/kg) | 393.29 L/h/m² (15 mg/kg) 89.46 L/h/m² (20 mg/kg) 29.56 L/h/m² (50 mg/kg) | 22.69 ± 4.14 mg * h/L (15 mg/kg) 133 ± 20 mg * h/L (20 mg/kg) 5031.61 ± 927.4 mg * h/L (50 mg/kg) | Sun, Yin, Wang |
| 50 mg/kg | Oral | 1181.17 ± 47.1 ng/ml | 1.5 ± 0.9 h | $3.1 * 10^{-3}$ L/h 9.22 L/h/m² | 16132.95 ± 5128.0 mg * h/L | Wang |

Table 7 shows a comparison of PK parameters for MMC from this and other studies:

TABLE 7

| Dosage | Administration Route | $C_{max}$ | $t_{max}$ | Clearance | AUC (Plasma Curves) (ng * min/ml) | Reference |
|---|---|---|---|---|---|---|
| 6 mg/kg | Intravesical | 32.19 ng/ml | 0.25 h | 44.002 L/h | 0.0273 mg * h/L | Current Study |
| 6 mg/kg | Oral | 53.28 ng/ml | 0.5 h | 41.790 L/h | 0.0287 mg * h/L | Current Study |
| 6 mg/kg | Intravenous | 39.5 ng/ml | 0.25 h | 58.344 L/h | 0.0206 mg * h/L | Current Study |
| 6 mg/kg | Intravesical, Drug-loaded MSN | 0.04 ng/ml | 1 h | 24000.00 L/h | $0.05 * 10^{-3}$ mg * h/L | Current Study |
| 6 mg/kg | Oral, Drug-loaded MSN | n/a | n/a | n/a | n/a | Current Study |
| 6 mg/kg | Intravesical + Oral, Drug-loaded MSN | 56.67 ng/ml | 3 h | 20.08 L/h | 0.0598 mg * h/L | Current Study |
| 4-5 mg/kg | Intravenous | 800 ng/ml (4 mg/kg) 12.8 ± 0.4 µg/ml (5 mg/kg) | 0.25 h (4 mg/kg) 0.083 h (5 mg/kg) | 3.93 ± 0.32 L/h (4 mg/kg) 59.49 L/h/m² (5 mg/kg) | 1.02 ± 0.1 mg * h/L (4 mg/kg) 10.07 ± 0.31 µg * h/L (5 mg/kg) | Li, Fang |
| 4-5 mg/kg | Intravenous, drug-loaded lipidic particles | 4250 ng/ml (4 mg/kg) 11.5 ± 0.4 µg/ml (5 mg/kg) | 0.25 h (4 mg/kg) 0.083 h (5 mg/kg) | 0.08 ± 0.01 L/h (4 mg/kg) 29.75 L/h/m² (5 mg/kg) | 49.05 ± 4.5 mg * h/L (4 mg/kg) 18.82 ± 0.51 µg * h/L (5 mg/kg) | Li, Fang |

These initial concentrations values are 55649.38 ng/mL, 16638.24 ng/mL, and 29498.07 ng/mL for Gemcitabine, Docetaxel, and mitomycin c, respectively. The concentrations drop off rapidly at 30 minutes and 1 hour following administration. One of the sample (8), the 3 h time point for intravesical administration, had insufficient volume for measurement in LC-MS. In plasma, Cmax values were also achieved in the first 15 minutes after administration. These values are 516.22 ng/mL for gemcitabine (~1% of Cmax for urine), and 32.19 ng/mL for mitomycin c (~0.1% of Cmax for urine). Interestingly, Docetaxel was below the detection threshold in plasma at every time point collected. The drugs were also detected in the stools at both 6- and 24-hours following administration, with Gemcitabine having a Cmax of 2.23 ng/mL at 24 h, Docetaxel having a Cmax of 9.44 ng/mL at 24 h, and Mitomycin C having a Cmax of 94.22 ng/mL at 6 h following administration. These values are considerably lower than plasma and urine, and gemcitabine in particular was only slightly above the LC-MS detection threshold.

The following discusses controlled drug release. Particles were coated using Kollicoat methacrylic acid ethylacrylate (MAE), a polymeric enteric coating designed to prevent release of the drug within the highly acidic environment of the stomach, offering protection to healthy cells. Tables 8 and 9 show release rates of encapsulated delayed) and capsulated particles delay release with either a lipid bilayer or a Kollicoat MAE. More specifically, Table 8 shows the average drug release of particles coated with a lipid bilayer. Lipid bilayer was formed using 8.99 mg DPPC, 1.22 mg Cholesterol, and 0.79 mg DSPE-PEG.

TABLE 8

| Drug | Delay of Release | Average Drug Release (µg/ml/min) |
|---|---|---|
| Gemcitabine | 4 hours | 1.91 ± 0.55 (n = 4) |
| Mitomycin C | Under 1 hour | 0.11 ± 0.06 (n = 2) |

Table 9 shows encapsulation of the particles and delayed release. Drug loading and release from MSN encapsulated with Kollicoat methacrylic acid ethylacrylate (MAE). MAE ranged from 0.3 to 3.0 mg for every 1 mg of MSN. Drugs were chosen for clinical current standard of care in bladder cancer.

TABLE 9

| Drug | Delay of Release | Average Drug Release (pg/ml/min) |
|---|---|---|
| Gemcitabine | 10 to 16 hours | 3.47 ± 1.34 (n = 2) |
| Mitomycin C | 5 hours | 2.55 ± 1.04 (n = 3) |
| Docetaxel | <1 hour to 24 hours | 1.57 ± 0.89 (n = 4) |

Overall, particles coated with MAE appear consistently to have longer delays. In the case of gemcitabine, it may take up to 16 hours for the drug to begin releasing. However, the rate of release appears to be much quicker. This indicates a possible burst release. Further PK analysis of samples taken at a later period reveal increased concentrations several hours after administration.

When delivered intravesically, delayed delivery is critical as the particles need to bind to the tumor, penetrate and then release its chemotherapeutic doses. Our rat model consistently confirmed the delay by PK measurements and the impact on cancer growth by imaging.

The following discusses imaging studies, which show evidence of deep MSN particle penetration into the muscular layer.

A consistent and reliable documentation of the state of the tumor growth over precise time points non-invasively in various animal species has been shown. In this rat model, subjects were imaged to verify tumor engraftment. In addition, following treatment, tumor growth abatement has been accurately/numerically documented (non-invasively and repeatedly). This is attainable only owing to the animal size combined with computational imaging and signal-enhancing properties our particles co-crystallization with contrast agents. The MSN provides augmented discriminatory contrast/resolution between normal and diseased tissue. In addition, rat computational imaging allows for the demonstration of deep penetration of the particles as evidenced by intensity measurement in the muscular layer on the bladder. This evidence further indicates that drugs carried within the particles have a close-range release impact on the muscle-invasive form of the tumor.

The contrast agents can be covalently linked to the MSN particles. A wide variety of contrast agents can be used, for example, these can consist of or comprise of a heavy metal (e.g., Au), gadolinium, lanthanide, a fluorophore, or a surface modification agent detectable with ultrasound.

Figure 4:
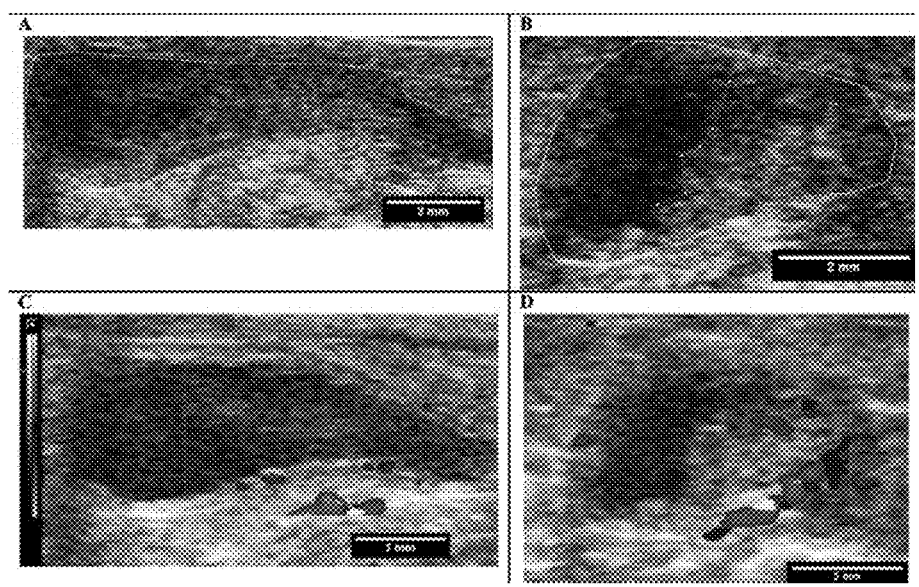
FIG. 4 shows Ultrasound and Doppler images evidence of Rat model instillation of bladder cancer cells and blood flow. The commensurate blood flow with the size of the tumor can be used as measure of successful engraftment and treatment.

Furthermore, tumor confirmation can be done by ultrasound: as early as 4-7 days following tumor engraftment. For this, surface modifications such as triflurocarbon (TFC) allows for rapid monitoring of tumor as seen (FIG. 4).

The following discusses oral administration and detection of the drug delivered orally. There is a need for oral drug delivery, i.e., it facilitates self-medication, storage, and reduced burden on the clinician, allowing for remote monitoring. An oral presentation for the treatment of bladder cancer using an engineered nanoparticle-drug treatment is a potentially innovative option for the treatment of BC. A similar methodology could be used to a multitude of other cancers/diseases.

Cmax values in the plasma are 636.02 ng/mL for Gemcitabine, 10.64 ng/mL for docetaxel, and 53.28 ng/mL for mitomycin C (FIG. 5). Tmax is reached at 30 minutes for Gemcitabine and mitomycin c, and 1 h for Docetaxel. Additionally, 1 h was the only time point in which docetaxel was above its detection threshold. In urine, Gemcitabine had a Cmax of 4737.26 ng/mL and a tmax of 1 h, Docetaxel reached a Cmax of 413.17 ng/mL and a tmax of 1 h, and mitomycin c reached Cmax of 16135.89 ng/mL with a tmax of 30 minutes. In the stool, Cmax values were all attained at 6 h following administration, and were 26.07, 351.52, and 157.09 ng/mL for Gemcitabine, Docetaxel, and Mitomycin C, respectively.

In this prototype experimentation, the drugs tested were the best options for MSN-drugs as it reflects the current standard of care, see O'Donnell (Urol Clin North Am. 47(1):83-91.). We compared the one or 2 drugs to experiment carried out intravenous/systemic and/or intravesicular drug alone.

The following discusses human bladder cancer cells instilled into athymic rats and studies of a rat xenograft.

Several novel drugs are consistently being discovered but in vivo effectiveness and potential toxicity is still debated and needs to be addressed prior to clinical trials. The best option is the use of xenograft of human cancer cells administration into animal subjects. In this disclosure, as an example, we used an athymic rat model. Eight week old female athymic nude rats (Inotiv Hsd:RH-Foxn1 rnu) were implanted with human male bladder cancer cell lines T24 or UMUC-3. The tumor take rate for first instillation was 1/6, or 17%, and 0/6 for reinstallation. Nine instillations were attempted using UMUC-3 cells (6 first instillation, 3 reinstallation), with one tumor reaching levels of growth for treatment. Three rats were reinstalled with T24 cells, with none forming tumors. The rat that formed a measurable, treatable tumor was treated 3× with intravesical chemotherapy, presenting a complete response in 32 days undetectable with high resolution ultrasound (20 MHz). The Doppler images show the vasculature signal has vanished along with tumor itself.

Artificial intelligence (AI) in the context of bioinformatics and nano-scale drug delivery imaging can also be used. AI as a generic expression encompasses areas of computer sciences such as machine learning, natural language processing (NLP) and artificial neural network (ANN). These technologies provide machines human-like intelligence to simplify and enhance complex data into discernment/diagnostic decision-making assets. In biomedical research AI-enabled computational and imaging methods have propelled pharmaceutical discovery. Algorithms can identify statistical patterns that ANN recognizes as "local behavior" of the imaged materials which leads to simplified diagnosis and prognosis. The particles-based treatment disclosed herein enhances signal and discriminatory elements which can be used to further compare normal to disease states automatically.

Precise nanoscale targeting enhances the contrast between diseased and normal tissue which empowers computational intelligence. Ultimately, these tools will undoubtedly push the frontiers of treatment to levels not yet envisioned. This disclosure affirms a clear and contrasted monitoring imaging and proof of effective tumoricidal outcomes. AI is based on enhanced contrasted events, our particle in this rat model and conditions may contribute to yet unknown innovations.

The following discusses the demonstration of individual differences. Experimentation in this disclosure validates subject-based variability, maybe an important model to evaluate response to pilot treatments. Given the same tumor implantation (verified by imaging), each animal responded differently: from no response (tumor continues growing) to complete remission. The tumor grafting success for first instillation in the normal rat was 16/18, or 89%, and 0/2 for reinstallation. For athymic nude rats, the tumor take rate for first instillation was 1/6, or 17%, and 0/6 for reinstallation. Nine instillations were attempted using UMUC-3 cells (6 first instillation, 3 reinstallation), with 1 tumor growing to the level of being treated. Three rats were reinstalled with T24 cells, with none forming tumors. This phenomenon has been consistently reported in bladder cancer clinical cases and other cancers. The genomics heterogeneity and limitations of tumors is the underlying individual variability and is the base for personalized or precision medicine. Optimal therapeutic drug choice could potentially be tailored to a particular individual/patient. Celik et al refers to an oncogram in bladder cancer cell testing together with clinico-pathological features may be a determining for pre-treatment drug selection (Celik, Per Med. 2023 May 17.). The literature there is abundant evidence that in non-systemic therapy bladder cancer has the potential to develop further in 25% of the patients, and into a fatal disease in 1 in 10 patients. Thus, the need for further refinement of prognostic and predictive genomic markers (Pietzak, Eur. Urol 72:952-9). This rat model is perfectly suited for studies of individually calibrated treatments based on in-depth onco-genetic data.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

We claim:

1. A method of treatment of a tumor comprising the steps of:
   administering to a patient a first pharmaceutical composition and a second pharmaceutical composition;
   wherein the first pharmaceutical composition comprises a mesoporous silica nanoparticle ("MSN"), a first bioactive agent comprising a first chemotherapeutic agent loaded into the MSN, a first coating encapsulating the surface of the MSN, and a targeting peptide or an amino acid covalently linked to the MSN;
   wherein the second pharmaceutical composition comprises an MSN, a second bioactive agent comprising a second chemotherapeutic agent loaded into the MSN, a second coating encapsulating the MSN, and a targeting peptide or an amino acid covalently linked to the MSN; and
   wherein the first bioactive agent is distinct from the second bioactive agent and the first chemotherapeutic agent and the second chemotherapeutic agent are chemically incompatible such that interaction between the two results in a reduction in effectiveness; and wherein the first pharmaceutical composition comprising the first chemotherapeutic agent and the second pharmaceutical composition comprising the second chemotherapeutic agent act upon a tumor sequentially or substantially concurrently without chemically interacting with each other.

2. The method of treatment of claim 1, wherein the first pharmaceutical composition is administered orally and the second pharmaceutical composition is administered intravesically.

3. The method of treatment of claim 2, wherein the first coating comprises enteric coating and the second coating comprises a gelatin, polymer, or a synthetic phospholipid bilayer.

4. The method of treatment of claim 3, wherein the administration of the first pharmaceutical composition and the second pharmaceutical composition being administered concurrently such that non-invasive and invasive tumors are addressed sequentially or substantially concurrently.

5. The method of treatment of claim 4, wherein the first pharmaceutical composition and the second pharmaceutical composition each comprise a contrast agent covalently linked to the MSN.

6. The method of treatment of treatment of claim 5, further comprising non-invasively monitoring a size of a tumor by imaging the first pharmaceutical composition and the second pharmaceutical composition as each are metabolized.

7. A method of treatment bladder cancer comprising the steps of:
   administering intravesically to a bladder of a patient a first pharmaceutical composition comprising of a mesoporous silica nanoparticle ("MSN"), a first bioactive agent loaded into the MSN, a first coating encapsulating the surface of the MSN, and a targeting peptide or an amino acid covalently linked to the MSN;
   administering orally to the patient and concurrently with the intravesicular administration of the first pharmaceutical composition to the bladder of the patient a second pharmaceutical composition comprising an MSN, a second bioactive agent loaded into the MSN, a second coating encapsulating the MSN, and a targeting peptide or an amino acid covalently linked to the MSN; and
   wherein the first bioactive agent is distinct from and chemically incompatible with the second bioactive agent; and wherein the first pharmaceutical composition and the second pharmaceutical composition act upon a tumor sequentially or substantially concurrently without chemically interacting with each other.

8. The method of treatment of claim 7, wherein the first coating comprises enteric coating and a second coating comprises a gelatin, polymer, or a synthetic phospholipid bilayer.

9. The method of claim 7, wherein the first pharmaceutical composition comprises a contrast agent covalently linked with the polymeric enteric coating to the MSN, wherein the contrast agent comprises at least one of a heavy metal, gadolinium, lanthanide, a fluorophore, and a surface modification agent detectable with ultrasound.

10. The method of claim 9, wherein the contrast agent is selected from the group consisting of a heavy metal, gadolinium, lanthanide, a fluorophore, and a surface modification agent detectable with ultrasound.

11. The method of claim 7, wherein the MSN is less than or equal to 200 nm in diameter with a mean pore diameter of about 2-3.8 nm for loading the bioactive agent.

12. The method of claim 7, wherein the bioactive agent is a chemotherapeutic agent or an immunogenic substance.

13. The method of claim 7, wherein the bioactive agent is selected from the group consisting of cannabidiol, epirubicin, mitomycin-c, gemcitabine, and taxanes.

14. The method of claim 7, further comprising a targeting peptide or an amino acid covalently linked to the MSN, wherein the targeting peptide or amino acid is cancer cell specific and correlated with the bioactive agent.

15. The method of claim 14, wherein the wherein the targeting peptide or amino acid is a bladder cancer cell specific cyclic peptide (Cyc6).

16. The method of claim 7, wherein a polymeric enteric coating comprises methacrylic acid ethylacrylate.

17. The method of claim 7, wherein the MSN is covalently functionalized with at least one material selected from a heavy metal, gadolinium lanthanide, a fluorophore, and an agent detectable by ultrasound, wherein the MSN is encapsulated with enteric coating and covalently linked with a bladder cancer cell specific cyclic peptide Cyc6.

* * * * *